US00PP09069P

United States Patent [19]

Button et al.

[11] Patent Number: Plant 9,069

[45] Date of Patent: Mar. 7, 1995

[54] AGLAONEMA PLANT NAMED 'GREEN MAJESTY'

[75] Inventors: Richard J. Button, Miami; Ann E. Lamb, Lake Placid, both of Fla.

[73] Assignee: Sunshine Foliage World, Zolfo Springs, Fla.

[21] Appl. No.: 234,562

[22] Filed: Apr. 28, 1994

[51] Int. Cl.[6] ..... A01H 5/00

[52] U.S. Cl. ..... Plt./88.1

[58] Field of Search ..... Plt. 88.1

*Primary Examiner*—Howard J. Locker

*Attorney, Agent, or Firm*—Foley & Lardner

[57] ABSTRACT

An Aglaonema plant named 'Green Majesty' characterized by its large dark green leaves marked along the margins with silver-green, rapid growth, and tolerance to cold.

3 Drawing Sheets

The present invention comprises a new and distinct cultivar of Aglaonema, botanically known as *Aglaonema hybrida,* and referred to by the cultivar name 'Green Majesty'.

The new cultivar is a product of a planned breeding program carried out by the inventor Richard J. Button in Miami, Fla. The new cultivar is a product of a cross of unknown parentage.

The first act of asexual propagation of 'Green Majesty' occurred when offshoots and tissue culture of the new cultivar were taken in Palmdale, Fla., under the supervision of inventor Ann E. Lamb. That and subsequent asexual reproduction, both by tissue culture and offshoots, have clearly established that the combination of characteristics of the new cultivar disclosed herein are firmly fixed and are retained through successive generations of asexual reproduction.

The following observations, measurements and values describe plants grown in Zolfo Springs, Fla. under shadehouse conditions which closely approximate those generally used in horticultural practice.

The following traits have been repeatedly observed to be characteristics which in combination distinguish 'Green Majesty' from other Aglaonema, for example, the well known cultivar 'Silver Queen'.

1. The leaves of 'Green Majesty' are much wider and longer than 'Silver Queen', giving the plant a dense, full appearance.

2. The leaves of 'Green Majesty' have a broad central dark green area, and abundant silver-green marginal markings.

3. Plants of 'Green Majesty' grow rapidly, attaining marketable size in approximately 20% less time than 'Silver Queen'.

4. Plants of 'Green Majesty', unlike 'Silver Queen', show little or no foliar damage when exposed to low tempertures of 40° F. for approximately 3 hours.

All color references are measured against the Royal Horticultural Society Colour Chart. Colors are approximate as color depends on horticultural practices such as light level and fertilization rate, among others, without, however any variance in genotype.

In the photographic drawings,

Sheet 1 is a color photograph showing a top perspective view of 'Green Majesty'. The photograph is of a plant of 'Green Majesty' in a 26 cm pot approximately 69 weeks after planting a single 4 leaf cutting and grown under appropriate growing conditions.

Sheets 2 and 3 comprise color photocopies illustrating, in actual size, the adaxial surface of typical leaves of the new cultivar.

Colors are as accurate as possible with color illustrations of this type.

Origin: Seedling selected from a cross of unknown parentage.

Classification: *Aglaonema hybrida,* cv 'Green Majesty'.

Propagation: Asexual propagation either by division or tissue culture.

Plant: When a 4 leaf cutting of 'Green Majesty' is grown in a 26 cm pot for 69 weeks under appropriate growing conditions, the plant reaches a height of approximately 24 cm to 30 cm from the soil surface to the junction of the petioles of the last two (2) unrolled leaves, and a width of approximately 82 cm to 86 cm.

Stem:

*Growth pattern.*—The stem is erect in growth and approximately 1.9 cm to 2.2 cm in diameter 5.0 cm above the soil surface. Internode distance is approximately 1.0 cm to 2.0 cm, 3 cm above the soil.

*Color.*—Immature: 145 A-B mottled with 145 D. Mature: Where exposed to direct light, darker and greener than 137 B mottled with 145 C. The area of leaf attachment takes on an orange 163 A cast with age.

Petiole: The following information is based on the 4th expanded leaf from the apex.

*Growth pattern.*—The petiole has fleshy edges, referred to as wings, extending from the midrib and approximately 3 mm to 5 mm in width one-half the distance from the petiole base to the wing apex. The wings extend from the base of the petiole to within approximately 1.5 cm to 2.5 cm of the base of the leaf. The apex of the wings is rounded, and often dried and brown. The petiole follows the stem axis but diverges from the axis approximately 12.5 cm to 14.5 cm from the leaf base, forming a horizontal distance from the edge of the stem to the leaf base of approximately 7.0 cm to 9.5 cm.

*Dimensions.*—The petiole is straight from its base to the tip of the wings, and curved outward from the tip of the wings to the base of the leaf. The petiole is approximately 8 mm in diameter one-half the distance between the top of the wing and the base of the leaf, and approximately 17 cm in length.

*Color.*—The petiole color is greener than, but closest to, 139 D, and streaked and mottled with 137 D. The base of the petiole often takes on an orange 163 D cast with age. The petiole wings are darker and greener, but closest to 138 A and streaked and mottled with 139 D. The lower edge of the petiole wings take on an orange 163 C D cast with age.

Leaf:

*Growth pattern.*—The leaf is ovate with an acuminate apex and an obtuse base. The margin is entire. The leaf is asymmetric with the side of the leaf unrolling first having less surface area than the side unrolling last. The leaf is oriented parallel to the stem axis at the time of full unrolling, changing to approximately 45 degrees to the stem axis as more leaves unroll above it. The midrib is straight, or curved downward. The leaf blade is flat or somewhat wavy from the midrib to the margin, and often wavy along the margin.

*Dimensions.*—For the pot size and growing time indicated, the largest leaves are approximately 30 cm to 31.5 cm long and approximately 12 cm to 13.5 cm wide. Average sized leaves are approximately 24 cm to 26 cm long and approximately 10.0 cm to 11.5 cm wide. The leaf is moderately thick.

*Midrib.*—The midrib is thick and prominent, recessed on the upper leaf surface and protruding from the lower surface. The color of the midrib on the upper surface is greener than, but closest to, 137 A on new leaves, and much darker and greener than, but closest to, 137 A on mature leaves. The color of the midrib on the lower surface is greener than, but closest to, 146 C-D on new and mature leaves. The junction of the leaf blade and midrib on the lower leaf surface is mottled with 145 D.

*Primary veins.*—The primary veins are sunken into the upper surface and protrude slightly from the underside. The primary veins on the upper surface are the same color as the tissue surrounding them. The primary veins are 137 A, often lightly mottled with 147 C on the lower surface.

*Color and pattern.*—The upper leaf surfaces give the general appearance of having a broad, dark green central band bordered by silver-green marginal markings. However, upon close observation, the central dark green band is overlaid by a mosaic of diffuse silver-green flecks. The marginal silver-green bands are made up of two shades of silver-green blotches.

*Colors.*—Central dark green markings: New leaf: Darker than, but closest to, 137 A, with diffuse flecks of 191 A. Mature leaf: Darker and greener than, but closest to, 139 A, with diffuse flecks of 189 A. Marginal silver-green markings: New leaf: 191 C with blotches of 189 A. Mature leaf: Darker and more silver than, but closest to, 191 A, with blotches of 189 A. The lower leaf surfaces are lighter and greener than, but closest to, 137 C on new leaves, and 137 C on mature leaves.

*Axillary breaks.*—There are approximately 16 axillary breaks with at least one leaf expanded. Leaves will show true color and pattern by the first leaf.

*Inflorescence.*—Typical of Aglaonema and does not have commercial significance.

Roots: Thick white roots with fine laterals.

General observation: Aglaonema 'Green Majesty' has large leaves marked along the margins with silver-green, and in the center with dark green. The plants grow rapidly, and tolerate temperatures to as low as 40° F. for at least three hours without noticeable foliar damage. These combined characteristics make 'Green Majesty' a unique new cultivar.

We claim:

1. A new and distinct cultivar of Aglaonema plant named 'Green Majesty', as illustrated and described.

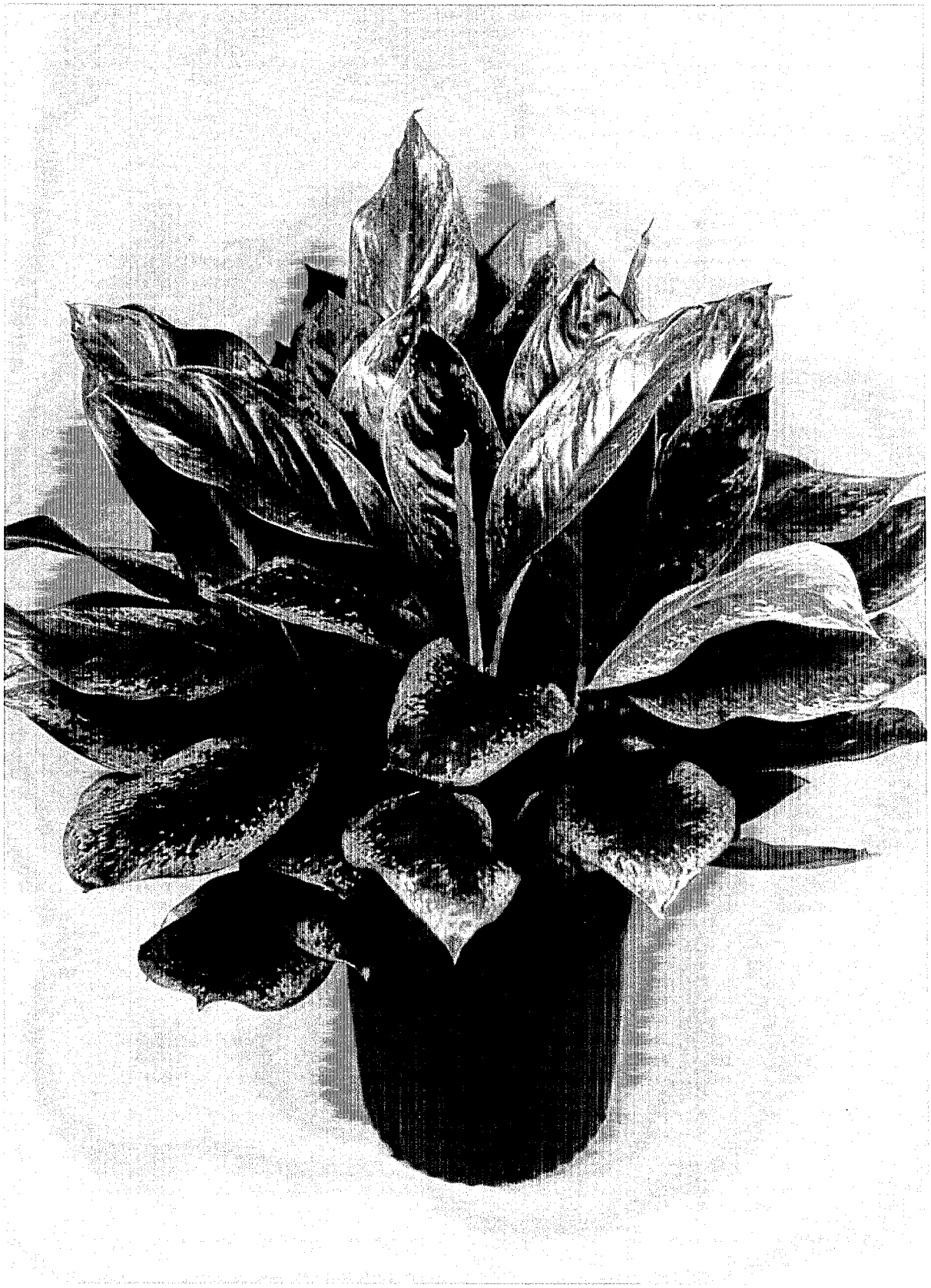

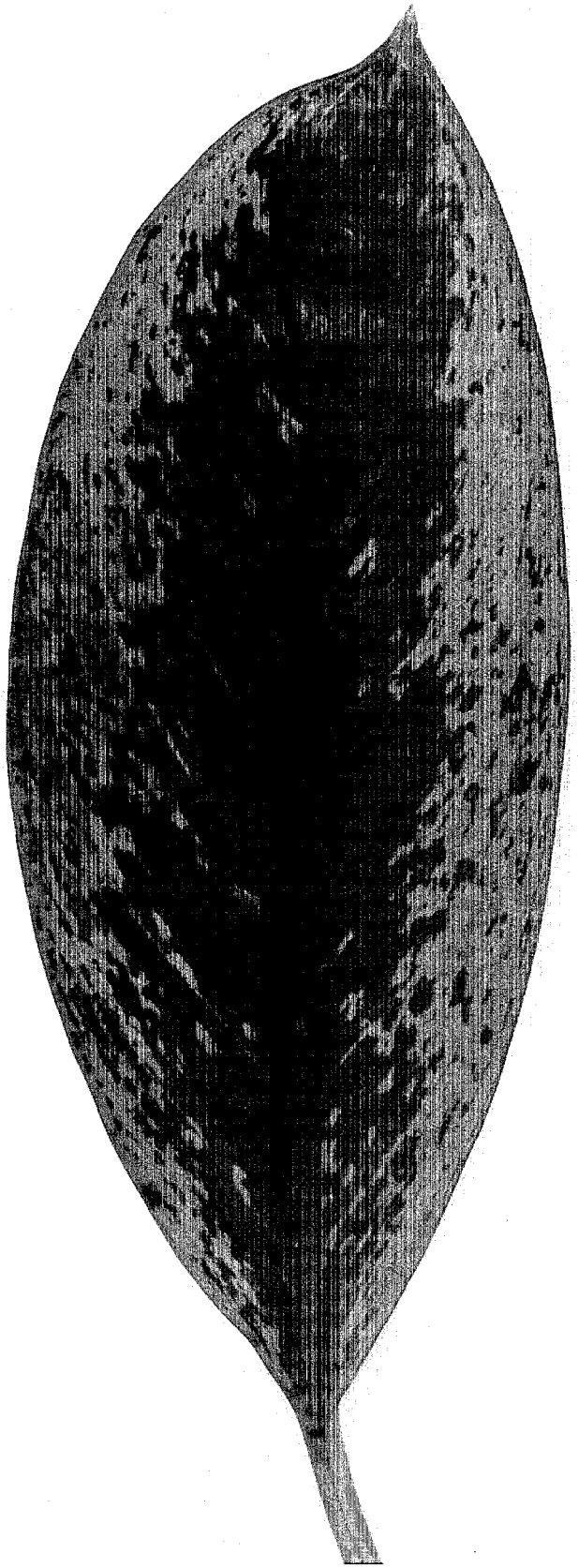

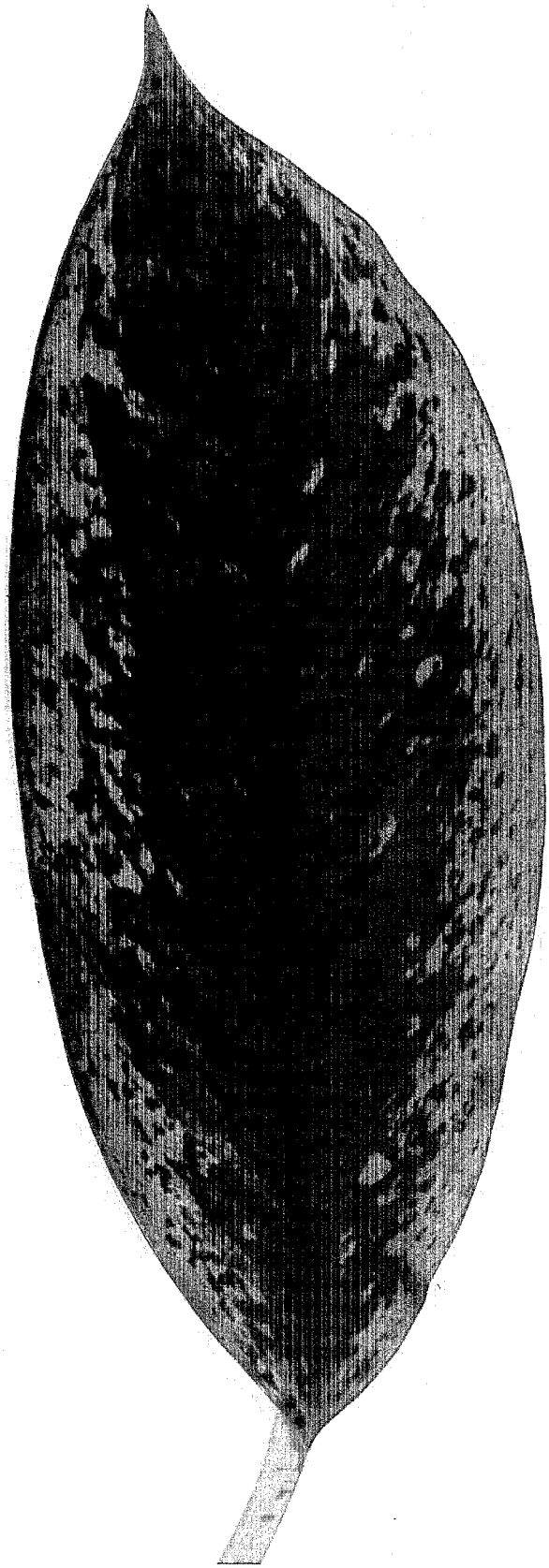

* * * * *